United States Patent [19]

Sones et al.

[11] Patent Number: 4,792,900
[45] Date of Patent: Dec. 20, 1988

[54] ADAPTIVE FILTER FOR DUAL ENERGY RADIOGRAPHIC IMAGING

[75] Inventors: Richard A. Sones, Cleveland Hts.; Karen L. Lauro, S. Euclid, both of Ohio

[73] Assignee: Picker International, Inc., Highland Hts., Ohio

[21] Appl. No.: 935,282

[22] Filed: Nov. 26, 1986

[51] Int. Cl.$^4$ .............................................. G06F 15/42
[52] U.S. Cl. .............................. 364/413.23; 378/99; 382/6; 382/54; 358/111
[58] Field of Search ....................... 364/414; 378/5, 99, 378/901, 156; 382/6, 52, 54, 62; 358/111, 166, 167

[56] References Cited

U.S. PATENT DOCUMENTS

| | | | |
|---|---|---|---|
| 4,458,267 | 7/1984 | Dolazza | 358/111 |
| 4,463,375 | 7/1984 | Macoyski | 358/111 |
| 4,499,493 | 2/1985 | Nishimura | 358/111 |
| 4,503,461 | 3/1985 | Nishimura | 358/111 |
| 4,546,255 | 10/1985 | Knoll et al. | 250/369 |
| 4,570,224 | 2/1986 | Shimoni et al. | 364/414 |
| 4,682,291 | 7/1987 | Reuveni | 364/414 |
| 4,707,786 | 11/1987 | Dehner | 364/414 |

OTHER PUBLICATIONS

"Hybrid and Cardiac DSA Systems" by S. Fox et al., pp. 387–394, AAPM Medical Physics Monograph No. 12, 1984.
"Noise Cleaning" by Pratt, Digital Image Processing, 1978, pp. 319–321.
"Generalized Image Cobminations in Dual KVP Digital Radiography" by Lehmann et al., Med. Phy. 8(5), Sep./Oct. 1981, pp. 659–667.
"Measurement-Dependent Filtering: A Novel Approach to Improved SNR" by A. Macovski et al., IEEE Transactions on Medical Imaging, vol. M1-2, No. 3, Sep. 1983, pp. 122–127.
"Single Slit Digital Radiography" by Mike Tesic et al., AJR:142, Apr. 1984, pp. 697–702.
"Detector for Dual Energy Digital Radiography" by Barnes et al., Radiology, No. 2, 1985, pp. 537–540.
"One Shot Dual Energy Subtraction Imaging" by Ishigaki et al., Radiology 1986; 161: pp. 271–273.

Primary Examiner—Jerry Smith
Assistant Examiner—Allen MacDonald
Attorney, Agent, or Firm—Fay, Sharpe, Beall, Fagan, Minnich & McKee

[57] ABSTRACT

A radiographic scanner (A) generates a high energy image representation which is stored in a high energy image matrix (V) and a low energy image representation which is stored in a low energy image memory (U). A pair of filter functions selecting circuits (C) select a first or soft tissue specific filter function and second or bone specific filter function, respectively. The soft tissue filter function selecting circuit selects and adjusts the soft tissue filter function in accordance with the pixel value of the low energy image representation for each corresponding pair of pixel values. Convolvers (44, 46) convolve pixel values from the high and low energy image representations with the selected and adjusted filter functions. A soft tissue transform function (48) transforms the filtered high and low energy image representations into a soft tissue or other material specific image representation (42). The other filter selecting and adjusting circuit selects and adjusts the bone specific filter functions which are convolved with the high and low energy image representations by convolvers (54, 56). A bone specific transform function (58) transforms the filtered high and low energy image representations into a bone basis image.

21 Claims, 3 Drawing Sheets

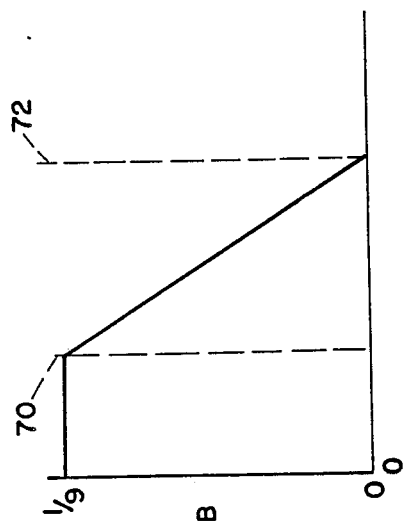
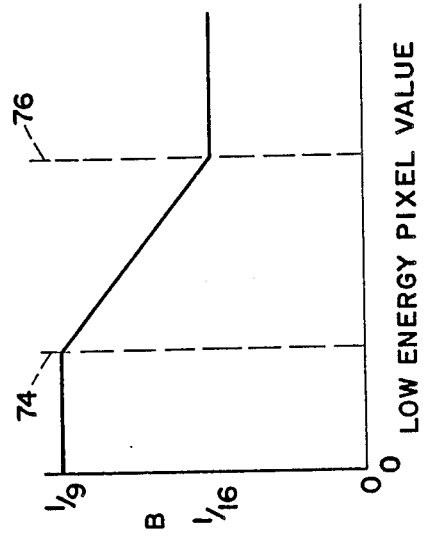
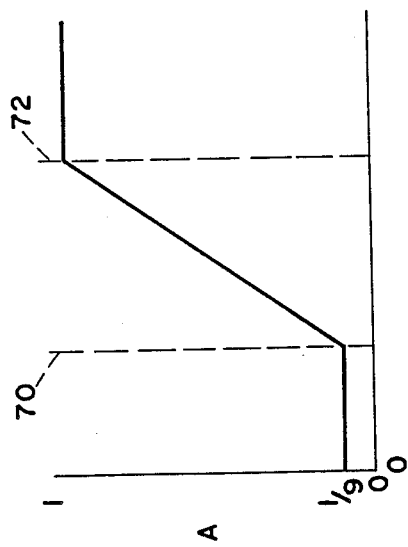
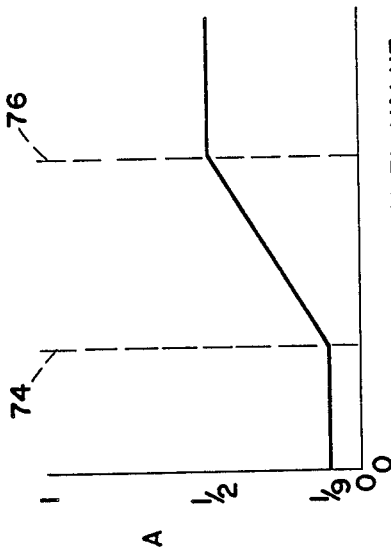

ADAPTIVE FILTER FOR DUAL ENERGY RADIOGRAPHIC IMAGING

TECHNICAL FIELD

This invention relates to the art of diagnostic imaging. It finds particular application in conjunction with dual energy, medical diagnostic digital radiography and will be described with particular reference thereto. However, it is to be appreciated that the invention may find further application in conjunction with other imaging techniques such as computed tomography and the like.

BACKGROUND ART

In a conventional film radiography system, an x-ray source directed a divergent beam of x-rays through a patient. After passing through the patient, the x-ray beam irradiated a phosphorescent screen as well as a light and x-ray sensitive film positioned adjacent the screen. As the radiation passed through the patient, it was attenuated in accordance with the tissue through which it passed to produce a shadow image on the film. The radiologist examined the gray scale, i.e. the light and dark regions, of the film directly for diagnostic purposes.

In digital radiography, the gray scale of each pixel or incremental region of the image was represented by an electronic, digital value. These digital values were processed by various data processing and image enhancement techniques to improve the diagnostic value of the image. Various techniques have been developed for digitizing film and other shadowgraphic images to derive the electronic digital values.

In one prior art digital radiographic technique, the digital values were derived directly from photographic film using a photodensiometer, video camera, or the like. In another prior art technique, a phosphor with a long term memory temporarily recorded the shadowgraphic image. A photo-sensitive apparatus converted the phosphor luminescence into corresponding digital values on a pixel by pixel basis.

The intensity of x-ray beams traversing the patient have also been converted directly into electronic signals. An array of electronic radiation detectors was disposed opposite the patient to receive the x-rays passing therethrough. In one technique, often denoted as "scan or slit projection radiography", a thin fan beam of radiation passed through a narrow plane of the patient and impacted a linear array of x-ray detectors. The radiation fan and the detector array were moved transverse to the fan beam plane to scan a selected rectangular region of the patient.

In another direct detection technique, an "area" beam of radiation was directed through the entire rectangular region of interest simultaneously to impact upon a large rectangular detector array. The intensities detected by the detectors were digitized for appropriate data processing and display on a video monitor or the like.

The material or body tissue can be characterized by the difference in its attenuation of a high energy and a low energy x-ray beam. To improve the diagnostic value of radiographic images, images of the region of interest have been constructed from both high and low energy radiation. In KV switching, dual energy radiography, two time sequential images were taken, one with higher energy x-rays and the other with lower energy x-rays. In dual detector scanners, both images were taken simultaneously with back to back detectors, one of which was sensitive primarily to the lower energy x-rays and the other was sensitive primarily to the higher energy x-rays.

In the prior art dual energy digital radiography, both high energy and low energy electronic image representations were derived. Each representation commonly included a rectangular array of pixels, each pixel having a pixel value indicative of the degree of radiation attenuation or transmissivity through a corresponding path of the region of interest. The pixel value variations were commonly represented by gray scale variations in man-readable images. Utilizing the transform functions set forth in "Generalized Image Combinations in Dual KVP Digital Radiography," L. A. Lehmann, et al., *Medical Physics*, Vol. 8, No. 5, pages 659-667, September/October 1981, the high and low energy specific images were transformed into one or more material specific basis image representations. The Lehmann, et al. transform operated on the pixels of the high and low energy images that correspond to the same volumetric subregion of the region of interest to produce a corresponding pixel value of the material specific image. Most commonly, two basis images were generated— one for water or soft tissue and the other for bone or calcium. For calibration purposes, plexiglass was utilized to approximate water and soft tissue and aluminum was utilized to approximate bone and calcium. Other transformations, such as pixel by pixel subtraction of weighted high and low energy images, have also been utilized.

One of the problems with the Lehmann, et al. transformation was that it amplified the noise of the images, i.e. the basis images had a lower signal-to-noise ratio than either the high or the low energy images. The random noise degradation was particularly bad in the high x-ray attenuation or thick portions of the spine which were represented by relatively low pixel values.

Various techniques have been developed for operating on the soft tissue and bone specific basis images to reduce the effect of random noise. One technique was to convolve each pixel of the basis image with a smoothing or filter function that averaged each pixel value with a percentage of the average value of the surrounding pixels. One drawback of this technique was that it removed the apparent random noise in the dense bone regions of the image by blurring the entire image.

To avoid blurring all regions of the basis image, others have provided a region specific filter function. Random noise commonly appears as a speck of a different intensity from the surrounding areas, i.e. a pixel value that is much larger or smaller than the values of adjacent pixels. Specifically, the deviation between a pixel value and each of its surrounding neighbors was determined. If greater than a preselected deviation was observed, the blurring filter function was applied to that pixel of the basis image. If less than the preselected deviation was observed, no filtering was applied to that pixel.

One disadvantage of this selective filtering technique is that the deviation between neighboring pixel values was not always an indication of noise. Rather, the deviation may have been the result of a tissue or bone boundary, a thin blood vessel, or the like. This led to an averaging which tended to blur edges and obscure fine details of the filtered basis image. Other filtering and data processing techniques, such as edge enhancement techniques, other types of smoothing or filtering, and the like have also been performed on the resultant basis images.

In accordance with the present invention, there is provided a new and improved image enhancement method and apparatus which overcomes the above referenced problems and others.

SUMMARY OF THE INVENTION

In accordance with one aspect of the present invention, a method of diagnostic imaging is provided. First and second image representations of the same region of a subject are generated. In the preferred embodiment, one of the images is a higher energy x-ray image representation and the other is a lower energy x-ray image representation. Prior to operating on the first and second image representations with a transform function, such as the Lehmann, et al. transform function discussed above, the first and second image representations are each filtered. The first and second filtered image representations are then transformed with one or more transform functions to produce a corresponding number of composite images. If the Lehmann, et al. transform functions are selected, two composite images commonly known as a soft tissue basis image and bone tissue basis image are produced. Other transformations of the filtered first and second image representations, such as simple subtraction, weighted averaging, approximations of the Lehmann, et al. equations, and the like may also be utilized.

In accordance with another aspect of the present invention, a method of diagnostic imaging is provided. A generated image representation is defined by a plurality of pixels, each pixel having a pixel value. For one of the pixels, its pixel value is compared with a preselected criteria, such as a preselected pixel value amplitude. One of a plurality of preselected filter functions is selected in accordance with the comparison of the pixel value and the preselected criteria. The pixel values of said one pixel and adjacent pixels are filtered with the selected filter function to create a filtered pixel value for a corresponding pixel of a filtered image representation. The comparing, filter selecting, and filtering steps are repeated for each pixel of the image representation to produce the corresponding pixel values for the filtered image representation. In this manner, the filter function for each pixel is selected in accordance with that pixel's pixel value. This method finds particular application in conjunction with digital x-ray radiography techniques in which the signal-to-noise ratio decreases as the magnitude of the pixel value decreases.

In accordance with another aspect of the present invention, a method of medical diagnostic imaging is provided. First and second image representations of a common region of a patient are generated. Both the first and second image representations are operated on with (1) at first transform function and (2) a first filter function to create a filtered first composite image, preferably a soft tissue basis image. Both the first and second image representations are also operated upon with (1) a second transform function and (2) a second filtering function which is different from the first filtering function to create a filtered second composite image, preferably a bone basis image. In this manner, different filter functions are utilized in the generation of the bone and soft tissue indicative images.

In accordance with yet another aspect of the present invention, an apparatus for diagnostic imaging is provided. First and second image memories are provided for storing first and second image representations of the same region of interest of the patient. A filter means separately filters pixel values of the stored first and second image representations with a first filter function to generate first and second filtered image representations, respectively. A transform means transforms the pixel values of the first and second filtered image representations into a composite image. A composite image memory is connected with the transform means for storing the composite image.

In accordance with another aspect of the present invention, an apparatus for diagnostic imaging is provided. An image memory stores pixel values for each of a plurality of pixels. A filtering means operates on the pixel values of each selected pixel and pixels thereadjacent with a selectively alterable filter function. A filter function altering means alters characteristics of the filter function in accordance with the pixel value of each pixel to be filtered. In this manner, the filter function with which each pixel is filtered varies with its pixel value.

A primary advantage of the present invention is that it enhances electronic images and reduces noise degradation.

Another advantage of the present invention is that it adaptively filters the noisier regions of an image more than more noise free regions.

Noisier thick bone representing regions are filtered to remove noise while substantially noise-free regions representing the lungs are not blurred or filtered to assure their diagnostic integrity.

Still further advantages of the present invention will become apparent to others upon reading and understanding the following detailed description of the preferred embodiments.

BRIEF DESCRIPTION OF THE DRAWINGS

The invention may take form in various steps and arrangements of steps or in various components and arrangements of components. The drawings are only for purposes of illustrating a preferred embodiment and are not to be construed as limiting the invention.

FIGS. 2A and 2B illustrate a preferred filter function alteration scheme for the soft tissue image of FIG. 1;

FIGS. 3A and 3B illustrate a preferred bone tissue filter function altering scheme; and, FIG. 4 is an alternate embodiment to the system of FIG. 1 for producing a combined soft tissue and bone or "normal" image.

DETAILED DESCRIPTION OF THE PREFERRED EMBODIMENTS

Figure 1:
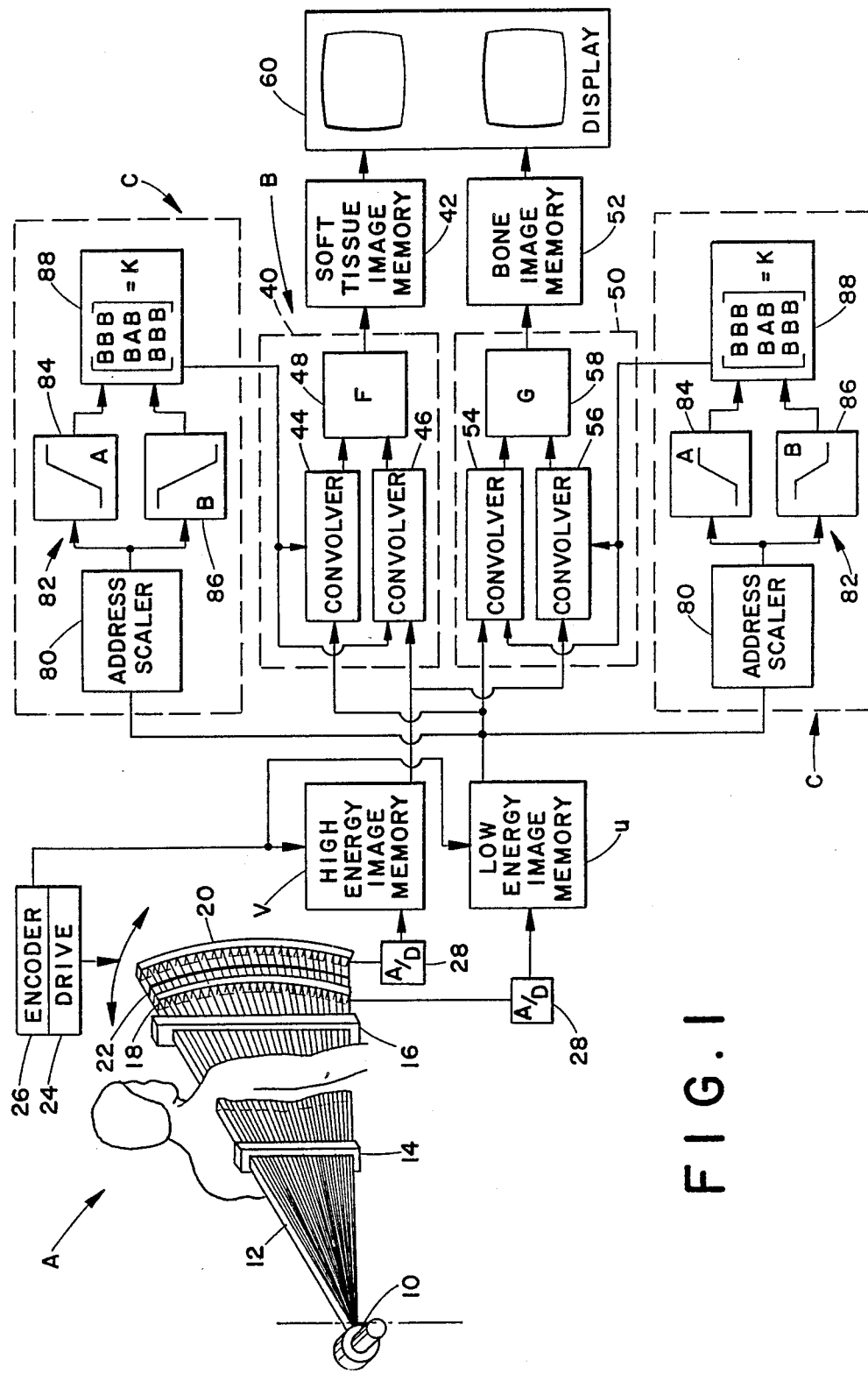
FIG. 1 is a diagrammatic view of a system for generating soft tissue and bone specific images from dual energy radiographic data in accordance with the present invention.

With reference to FIG. 1, a diagnostic scanner A such as a digital, x-ray slit scanner, a CT scanner, a magnetic resonance imager, or the like generates a pair of image representations of the same region of interest of a subject, e.g. a low energy image U and a high energy image V. An adjustable filter and transform means B converts the high and low energy images into one or more material specific or other composite images. A filter altering means C monitors at least one of the high and low energy images to determine the relative magnitude of the signal-to-noise ratio at each image pixel and alters the function applied in the filter and transform means B accordingly. The lower the signal-to-noise ratio is in a subregion, the more the pixel values representing the subregion are filtered or smoothed.

The scanner A illustrated in FIG. 1 for purposes of explanation is a slit scan projection type digital radiography system. It includes an x-ray source 10, such as an x-ray tube, which generates a polyenergetic fan beam 12 of x-rays having at least two energy levels. An entrance collimator 14 and an exit collimator 16 collimate the x-ray beam passing through the patient to be predefined fan shaped plane. A first or low energy detector array 18 includes a first linear array of detectors for detecting the low energy x-rays of the x-ray beam. A second or high energy x-ray detector array 20 includes a linear array of x-ray detectors disposed directly behind the low energy detector array to detect the high energy x-ray photons.

The stopping power of the low energy detectors is such that primarily low energy photons are stopped and transformed to electrical signals, while most high energy photons pass therethrough. The high energy detectors are configured of a denser higher atomic number material with more stopping power to stop and convert the high energy photons into electrical signals indicative of the intensity of high energy radiation impinging thereon. One detector for each of the high and low energy arrays are disposed in alignment back to back with the x-ray source such that a corresponding pair of the detectors detect high and low energy radiation which has traversed the same line or subregion of the patient. An x-ray absorptive material 22, such as a sheet of copper, absorbs middle energy x-ray photons that have sufficient energy to pass through the low energy detectors. The thickness of the copper sheet is selected to absorb photons whose energy is below a preselected high energy level. In this manner, relatively distinct and separated high and low energy photon levels are detected.

A mechanical drive 24 causes the high and low energy detector arrays and the entrance and exit collimators to be swept transverse to the plane of the beam such that a rectangular region of interest of the patient is irradiated. An encoder 26 changes the address for the low and high energy images U and V each time the detector array moves an incremental distance. In this manner, sweeping the detector array provides analogous data to a pair of rectangular high and low energy detector grids. Optionally, such detector grids may be provided with the elimination of the mechanical drive 24 and encoder 26 such that all pixels of the high and low energy images are collected simultaneously rather than column by column.

Each detector of the high and low energy detector arrays produces an analog electronic output signal which varies in proportion with the intensity of x-rays which it receives. In the preferred embodiment, each detector includes a scintillation crystal which scintillates or emits light in proportion to the intensity of the received radiation. A photodiode produces an analog output signal whose amplitude varies in accordance with the intensity of the light from the scintillation crystal. Detectors which convert the radiation directly into electrical signals, CCD devices, and other known radiation detectors are also contemplated. Analog to digital converters 28 convert the analog intensity signals into digital representations of the radiation intensity.

The high and low energy image representations are each defined by a rectangular array of pixels, corresponding to a rectangular array of subregions of the scanned region of interest. The digital pixel values corresponding to each pixel of the images or subregions of the region of interest are stored in corresponding memory elements of low and high energy image memories U and V. In the illustrated embodiment, one pixel in each column of the images corresponds to a corresponding detector in the detector array. Each time the detector array is swept an incremental transverse distance, the data for the next adjacent pixel column is generated. Because the detector arrays are back to back, each pixel in the low energy image representation has a corresponding pixel in the high energy image representation that represents the same subregion of the region of interest. In the preferred embodiment, subregions of the subject which attenuate radiation the most, such as dense bone, cause the scintillation crystals to generate less light, hence produce smaller analog signals and lower digital pixel values. Other numbering schemes for the pixel values may, of course, be utilized. The values may vary linearly, logrithmically, or with other preselected relationships with x-ray intensity.

The adjustable filter and transform means B includes a first material specific image filter and transform means 40 which filters and transforms the high and low energy images into a first or soft tissue specific image stored in memory 42. A first filter means convolves the low and high energy image representations separately pixel by pixel with an adaptive first filter function that varies from pixel to pixel to produce filtered low and high energy image representations. A first convolver 44 operates on the low energy image pixel values with the first filter function to produce the filtered low energy image representation. A second convolver 46 operates on each of the high energy image pixel values with the same first filter function as the corresponding low energy image pixel to generate the filtered high energy image representation. That is, the low energy image pixel value for the ith column and the jth row, U(i,j), and the high energy image pixel value for the same column and row, V(i,j), are each convolved with the same filter function K(i,j) to generate filtered values U'(i,j) and V'(i,j) corresponding to the (i,j)th pixel. Optionally, a filtered image memory means may be provided for storing the filtered high and low energy images from the convolvers 44 and 46.

A first transform means 48 operates on the filtered low and high energy image representations U' and V' with the first transform F to generate a selected material specific image I. That is, the material specific image I is a function F of the filtered high and low energy images, U' and V':

$$I = F(U', V') \quad (1)$$

Various functions F may be selected. As one example, each pixel value of the material specific image I may be the difference of the corresponding pixels of the high and low energy images:

$$I(i,j) = V'(i,j) - U'(i,j) \quad (2)$$

As yet another example, the material specific image may be other linear combinations of the filtered high and low energy images, such as a weighted averaging:

$$I(i,j) = \frac{m \, V'(i,j) + n \, U'(i,j)}{m + n}, \quad (3)$$

where m and n are weighting factors.

In the preferred embodiment, a transform analogous to the transform set forth by Lehmann, et al. is utilized. Each image of the material selected image is related logrithmically to the corresponding pixels of the filtered high and low energy images:

$$\begin{aligned} I(i,j) = {} & k_1 \log U'(i,j) + k_2 \log V'(i,j) + \\ & k_3 \log^2 U'(i,j) + k_4 \log^2 V'(i,j) + \\ & k_5 \log U'(i,j) \log V'(i,j), \end{aligned} \quad (4)$$

where $k_1$, $k_2$, $k_3$, $k_4$, and $k_5$ are constants which are determined for the given scanner A and for a selected material to which the image is to be selective in an initial calibration process. Due to the hardware constraints, the k constants will be different for each selected scanning apparatus. Moreover, different constants will be selected for a soft tissue selective image, a bone selective image, and other material selective images. Plexiglass may be utilized for an initial calibration to select the k constants for a soft tissue specific image and aluminum may be utilized as a calibration phantom to select the calibration constants k for a bone specific image.

A second material specific filter and transform means 50 filters and transforms the high and low energy images into a second, preferably a bone specific image stored in memory 52. A pair of convolvers 54 and 56 operate pixel by pixel on corresponding pixels of the high and low energy image representations with a second adaptive filter function $K_2$. The convolvers 54 and 56 perform a similar convolution as convolvers 44 and 46 except with a different filter function that is uniquely selected for the material specific image to be generated. A second transform means 58 operates on the filtered high and low energy images with a second transform G to transform them into a second material selective image, preferably a bone selective image I. A display means 60 selectively displays the soft tissue and bone specific images from memories 42 and 52. As discussed above, the function G may be a difference, weighted average, logrithmic combination, or other linear or non-linear combination of the corresponding pixels of the filtered high and low energy image representations. Preferably, the second transform G implements Equation (4) except that the values of the constants k are selected specifically for bone or aluminum rather than soft tissue or plexiglass.

Where appropriate, additional material specific filter/transform means may be provided for filtering and transforming the high and low energy images into images which are specific to other materials. Although the filter convolution and the transform are shown as separate operations, it is to be appreciated that some filter and transform functions may be combined into a single adaptive function to expedite data processing.

The filter altering means C projects the signal-to-noise ratio at each pixel of the image in accordance with the level of the pixel value and alters the filter function or the transform accordingly. The lower the pixel value, i.e. the greater the radiation attenuation, the greater the potential that the pixel value will include significant noise or be in a noisy region. As the pixel value increases, hence, the radiation attenuation decreases, the signal to noise level ratio improves and the amount of filtering is reduced.

In the preferred embodiment, the filter function K is defined by a $3 \times 3$ kernal matrix:

$$K = \begin{bmatrix} B & B & B \\ B & A & B \\ B & B & B \end{bmatrix}. \quad (5)$$

Convolving a given pixel value U(i,j) with this filter function, replaces the given pixel value with the sum of A times the given pixel value plus B times each of the eight immediately adjacent pixel values, i.e. the filtered image U' is defined by:

$$\begin{aligned} U'(i,j) = {} & AU(i,j) + BU(i-1,j-1) + BU(i-1,j) + \\ & BU(i-1,j+1) + BU(i,j-1) + BU(i,j+1) + \\ & BU(i+1,j-1) + BU(i+1,j) + BU(i+1,j+1) \end{aligned} \quad (6)$$

The values of A and B are selected in accordance with the magnitude of the given pixel value. The preferred embodiments of A and B for soft tissue are defined by the curve of FIGS. 2A and 2B.

With specific reference to FIGS. 2A and 2B, when the pixel value is below a preselected minimum threshold 70, about 2% of the pixel value dynamic range in the preferred embodiment, the region is assumed to be very noisy. Accordingly, A and B are each selected to be 1/9. That is, the pixel value is replaced with the average of itself and its eight surrounding pixel values. When the pixel value is above a preselected high threshold 72, preferably about 20% of the pixel value dynamic range, the pixel value is unchanged. That is, A=1 and B=0. In between the high and low threshold values, the relative magnitudes of A and B vary linearly with the pixel levels. In the embodiment illustrated in FIGS. 2A and 2B, the value of A varies linearly between 1/9 and one; the value of B varies linearly between 1/9 and zero.

With reference to FIGS. 3A and 3B, a different filter function is preferably selected for the soft tissue and bone specific images. Rather than the relationship illustrated in FIGS. 2A and 2B for soft tissue, the preferred values of A and B for a bone specific image are illustrated in FIGS. 3A and 3B. For low pixel values or high x-ray attenuation below a low threshold 74, each pixel is again averaged evenly with its surrounding neighbors. Above a preselected high threshold level 76, each pixel continues to be averaged with its surrounding neighbors. However, the value of A is selected at ½ and the value of B is selected at 1/16. Between the high and low threshold values, the value of A varies between 1/9 and ½ linearly and the value of B varies linearly between 1/9 and 1/16.

Other relationships between A and B may be selected. However, it is preferred that:

$$A + 8B = \text{constant} \quad (7)$$

In the illustrated embodiment, the constant is one. Other relationships between A and B may clearly be selected, for example, their values may change exponentially, logrithmically, or along other complex functions. For example, A and B may vary with a generally S-shaped curve in which A asymptotically approaches 1/9 at one extreme and 1 for soft tissue and ½ for bone at the other extreme; and B asymptotically approaches 1/9 at one extreme and zero for soft tissue and 1/16 of bone at the other extreme. This function may vary continuously over the full dynamic range of pixel levels without cut off thresholds.

Other filter functions or kernals K may also be selected. For example, the kernal may be other sizes, such as a 5×5 matrix which averages each pixel value with some fraction of the eight immediately surrounding pixel values and the sixteen next most immediately surrounding pixel values. Moreover, as the kernal matrix becomes larger, the pixel values within each surrounding ring may vary generally in accordance with its radial distance from the center rather than solely as a function of the square ring. Other convolution and filter functions may optionally be selected.

With reference again to FIG. 1, the preferred noise level determining and filter altering means C includes separate circuitry for each of the material specific images. This allows a different filter function, such as the filter function of FIGS. 2 and 3, to be selected for each material specific image. However, because each of the filter altering means C is of the same construction, it is to be appreciated that the following discussion applies equally to both.

Where appropriate, an address scaler means 80 may adjust the low energy pixel values U(i,j) to correspond to the addresses of a kernal or filter function selection means 82. Preferably, the low energy image representation is used to select the filter function for the corresponding pixels of both the low and high energy images. In a preferred embodiment, the filter function selection means includes a first look-up table 84 which is addressed by the first pixel value U(i,j) to look up the corresponding A value and a second look-up table 86 which is addressed by the pixel value to look up the corresponding B value. A kernal matrix means 88 assembles the kernal matrix or filter function K from the values retrieved from the look-up tables 84 and 86. If larger kernal matrixes are used, additional look-up tables may be provided for selecting the additional matrix values. Optionally, the filter function selection means 82 may be an arithmetic unit which calculates the A and B values mathematically from each pixel value U(i,j).

Figure 4:
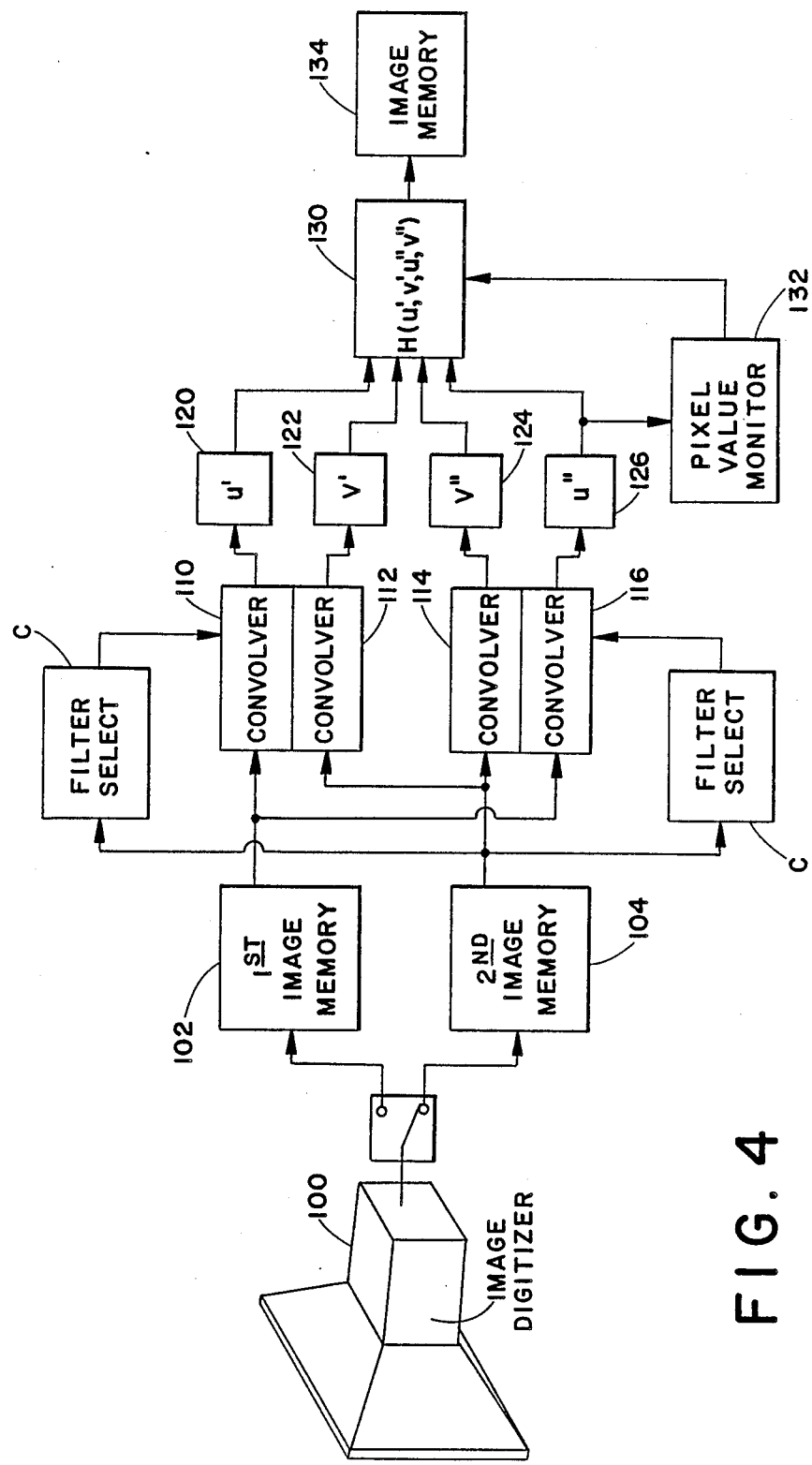

With reference to FIG. 4, the first and second or high and low energy images may be recorded at different times. An image digitizer 100 may convert a film, long term memory phosphor, or image intensifier output image into pixel values for corresponding pixels of a first or low energy image for storage in a first image memory means 102. Subsequently, a second film, phosphor, or image intensifier image taken through the same region of the patient may be digitized by the digitizer for storage in a second image memory 104. If the first and second film or phosphor images were taken with different energies of radiation, the first and second digital images will represent high and low energy images of the same region. Appropriate indexing to align the images may be required.

In accordance with the level of pixel values in the low energy or first image, filter function selecting means C select the appropriate filter functions for convolvers 110, 112, 114, and 116 which generate filtered images for storage in filtered image memories 120, 122, 124, and 126.

An adaptive transform means 130 combines the filtered images in accordance with the level of pixel values therein. A pixel value monitoring means 132 monitors the amplitude of pixel values of one of the images, preferably one of the filtered low energy images. Various transform functions may be selected. The image created by the transform means 130 is stored in a composite image memory 134. For example, the transform means 130 may sum corresponding pixel values of all four filtered images when the corresponding pixel value of the monitored image is in a preselected amplitude range, such as a central range. For low amplitude ranges, the corresponding pixels of the two filtered high energy images may be added. In between the central and low ranges, a weighted averaging may be performed. Analogously, in a high pixel amplitude range, the corresponding pixels of the low energy image might be added. Between the middle and high pixel value ranges, a ramp function or the like might be selected as a basis for performing a weighted averaging. Other combination equations are, of course, contemplated.

The invention has been described with reference to the preferred embodiments. Obviously modifications and alterations will occur to others upon reading and understanding the preceding specification. It is intended that the invention be construed as including all such modifications and alterations insofar as they come within the scope of the appended claims or the equivalents thereof.

Having thus described the preferred embodiments, the invention is now claimed to be:

1. A medical diagnostic imaging apparatus for producing soft tissue and bone specific basis images from dual energy radiation data, the apparatus comprising:

a radiation source for producing at least higher energy and lower energy radiation;

a radiation detection means for separately detecting the higher and lower energy radiation traversing a selected region of interest and for producing digital electronic values indicative of the intensity of higher and lower energy radiation received thereby;

a higher energy image memory means operatively connected with the detection means for storing the higher energy radiation intensity indicative digital electronic pixel values for each pixel for a higher energy image representation of the region of interest;

a lower energy image memory means operatively connected with the detection means for storing the lower energy radiation intensity indicative digital electronic pixel values for each pixel for a lower energy image representation of the region of interest;

a first convolver means for convolving a first filter function pixel by pixel with the digital values of the higher energy image representation and for convolving the first filter function pixel by pixel with the digital values of the lower energy image representation;

a first filter function altering means for correspondingly adjusting a characteristic of the first filter function in accordance with the digital value of each pixel of at least one of the higher and lower energy image representations;

a first transform means for transforming convolved values of corresponding pixels of the higher and lower energy representations into a digital gray scale value of a corresponding pixel of a soft tissue specific basis image;

a soft tissue image memory means operatively connected with the first transform means for storing the gray scale values of the soft tissue basis image;

a second convolver means for convolving a second filter function with the digital values of the higher energy image representation and convolving the second filter function with the digital values of the low energy image representation;

a second filter function altering means for correspondingly adjusting a characteristic of the second filter function in accordance with the digital value of each pixel of at least one of the high and low energy image representations; and, a second transform means for transforming convolved values of corresponding pixels of the higher and lower energy image representations from the second convolver means into a digital gray scale value of a corresponding pixel of a bone specific basis image.

2. An apparatus for producing diagnostic images, the apparatus comprising:

a first image memory means for storing an electronic pixel value for each pixel of a first image representation;

a second image memory means for storing an electronic pixel value for each pixel of a second image representation;

a first filter means for operating on each pixel value of the first image representation from the first memory means with a first filter function and for operating on each pixel value of the second image representation from the second memory means with the first filter function;

a first transform means for transforming filtered pixel values from the first and second memory means into a first composite image; and, a first composite image memory means for storing the first composite specific image.

3. The apparatus as set forth in claim 2 further including a first filter function altering means for selectively altering the first filter function in accordance with a statistical probability that the pixel to be filtered is free from noise degradation.

4. The apparatus as set forth in claim 3 wherein the filter function altering means includes at least one look-up table which is operatively connected with at least one of the first and second image memories to be addressed by the pixel value of at least one of each corresponding pair of pixels to be filtered, the look-up table retrieving kernal matrix values of a filter function in accordance with the addressing pixel value and wherein the first filter means includes a convolving means for convolving the first and second image memory pixel values with the kernal matrix.

5. The apparatus as set forth in claim 2 further comprising:

a second filter means for operating on each pixel value of the first image representation from the first memory means with a second filter function and for operation on each pixel value of the second image representation from the second memory means with the second filter function;

a second transform means for transforming filtered pixel values from the first and second memory means into a second composite image; and, a second composite image memory means for storing the second composite image.

6. The apparatus as set forth in claim 5 wherein the first and second image representations are radiation energy specific and the first and second composite images are irradiated material specific.

7. The apparatus as set forth in claim 6 further including a filter function altering means for selectively altering the first and second filter functions, the filter function altering means being operatively connected with one of the first and second image memories for altering the first or second filter function in accordance with each pixel value to be filtered by the filtering means.

8. An apparatus for diagnostic imaging comprising:

a first image memory which stores a plurality of pixel values, each pixel value corresponding to a pixel of an image representation;

a comparing means for comparing each pixel value from the first image memory with a preselected criteria;

a filter function altering means for selecting characteristics of a filter function for each pixel to be filtered in accordance with the comparison of the pixel value with the preselected criteria, the pixel value altering means being operatively connected with the comparing means; and, a first filtering means for operating on the pixel values of each pixel and pixels thereadjacent with the selectively altered filter function, the first filtering means being operatively connected to the first image memory, whereby the filter function with which each pixel is filtered varies in accordance with its pixel value.

9. The apparatus as set forth in claim 8 further including:

a second image memory for storing pixel values of a second image representation;

a second filtering means for operating on the pixel values from the second image memory for each pixel and pixels thereadjacent with the selectively altered filter function, whereby the filter function with which each second image memory pixel is filtered varies in accordance with the comparison of the pixel value of the corresponding pixel of the first image memory with the preselected characteristic;

a first filtered image memory means operatively connected with the first filtering means for receiving filtered first image pixel values therefrom;

a second filtered image memory operatively connected with the second filtering means for receiving filtered second image pixel values therefrom;

a transform means operatively connected with the first and second filtered image memory means for transforming the filtered first and second image pixel values into corresponding pixel values of a composite image representation; and, a composite image memory means operatively connected with the transform means for storing the composite image pixel values.

10. The apparatus as set forth in claim 9 further including a transform altering means for selectively altering the transform applied by the transform means, the transform altering means being operatively connected with at least one of the first and second filtered image memory means for selectively altering the transform in accordance with the pixel values thereof.

11. A method of diagnostic imaging comprising:
(a) generating first and second image representations of the same region of a subject;

(b) filtering the first image representation with a first filter function to produce a filtered first image representation;

(c) filtering the second image representation with the first filter function to produce a filtered second image representation; and, (d) transforming the filtered first and second image representations with a first transform function into a first composite image.

12. The method as set forth in claim 11 further including filtering the first and second image representations with a second filter function to produce second filter function filtered first and second image representations and transforming the second filter function filtered first and second image representations with a second transform function into a second composite image.

13. The method as set forth in claim 12 wherein the first and second image representations represent high and low energy specific radiographic images, respectively, and wherein the first and second transform functions transform the filtered image representations into images representative of a first material and a second material such that the first composite image is a first material specific image and the second composite image is a second material specific image.

14. The method as set forth in claim 11 wherein:

the first and second image representations are each defined by a plurality of pixels, each pixel of the first image representation having a corresponding pixel in the second image representation which represents the same subregion of an imaged region of interest, each image representation having a plurality of pixel values, each pixel value corresponding to one of the pixels, and further including altering the first filter function in accordance with a characteristic of each pixel value to be filtered such that the first filter function is varied in accordance with the pixel value of each pixel to be filtered.

15. A method of diagnostic imaging comprising:

(a) generating at least one image representation which is defined by a plurality of pixels each with an electronic pixel value;

(b) for one pixel, comparing at least its pixel value with a preselected pixel value criteria;

(c) in accordance with the comparison of step (b), selecting one of a preselected plurality of filter functions;

(d) filtering the pixel values of said one pixel and adjacent pixels with the selected filter function to create a filtered pixel value for a corresponding pixel of a filtered image representation;

(e) repeating steps (b) through (d) for other pixels of the image representation.

16. The method as set forth in clam 15 wherein each filter function includes a matrix and wherein the filter function selecting step includes selecting the values of matrix elements and wherein the filtering step includes convolving pixel values of the image representation with the matrix.

17. The method as set forth in claim 15 further including repeating steps (a) through (e) for a second image representation such that first and second filtered image representations are generated and transforming the filtered image representations into a plurality of composite images.

18. The method as set forth in claim 17 wherein the steps of generating first and second image representations include irradiating a common region of interest of a patient with radiation of first and second energy levels and measuring the intensity of radiation of each of the first and second levels traversing the region of interest and wherein the composite images include a soft tissue basis image and a bone basis image.

19. A method of medical diagnostic imaging comprising:

(a) generating first and second image representations of a common region of a patient;

(b) operating on both the first and second image representations with (1) a first transform function and (2) a first filter function to create a first composite image; and, (c) operating on both the first and second image representations with (1) a second transform function and (2) a second filter function which is different from the first filter function to create a second composite image.

20. The method as set forth in claim 19 wherein the image representation generating step includes irradiating the patient with radiation of a first energy level to generate the first image representation and irradiating the patient with radiation of a second energy to generate the second image representation and wherein the transform functions are selected such that the first composite image is material specific to soft tissue and the second composite image is material specific to bone.

21. The method as set forth in claim 19 further including adaptively altering at least one of the first filter and transform functions and altering at least one of the second filter and transform functions in accordance with characteristics of at least one of the first and second image representations.

* * * * *